(12) United States Patent
Gallagher

(10) Patent No.: US 10,617,802 B2
(45) Date of Patent: Apr. 14, 2020

(54) ASPIRATORS

(71) Applicant: ASPIRATE N GO LTD, Liverpool Merseyside (GB)

(72) Inventor: George Gallagher, Caerwys (GB)

(73) Assignee: Aspirate N Go Ltd., Liverpool, Merseyside (GB)

( * ) Notice: Subject to any disclaimer, the term of this patent is extended or adjusted under 35 U.S.C. 154(b) by 378 days.

(21) Appl. No.: 15/121,618

(22) PCT Filed: Feb. 25, 2015

(86) PCT No.: PCT/GB2015/050539
§ 371 (c)(1),
(2) Date: Aug. 25, 2016

(87) PCT Pub. No.: WO2015/128638
PCT Pub. Date: Sep. 3, 2015

(65) Prior Publication Data
US 2016/0361474 A1 Dec. 15, 2016

(30) Foreign Application Priority Data

Feb. 28, 2014 (GB) .................................. 1403597.6
Nov. 3, 2014 (GB) .................................. 1419542.4

(51) Int. Cl.
*A61M 1/00* (2006.01)
*A61M 39/10* (2006.01)
(Continued)

(52) U.S. Cl.
CPC ....... *A61M 1/0035* (2014.02); *A61B 5/14532* (2013.01); *A61B 5/14546* (2013.01);
(Continued)

(58) Field of Classification Search
CPC .... A61M 39/10; A61M 39/223; A61M 39/24; A61M 2039/2446; A61M 2039/244
See application file for complete search history.

(56) References Cited

U.S. PATENT DOCUMENTS 3,572,375 A    3/1971   Rosenberg
3,631,654 A * 1/1972   Riely .................... A61M 5/165
                                                                                96/6

(Continued)

FOREIGN PATENT DOCUMENTS

GB    2338898 A * 1/2000 .......... A61M 1/0023
WO   8700439 A1   1/1987

*Primary Examiner* — Adam Marcetich
*Assistant Examiner* — Jessica R Arble
(74) *Attorney, Agent, or Firm* — Blue Filament Law PLLC

(57) ABSTRACT

A valve assembly (50) comprising a three-way connector (51) operatively interconnecting: an inlet (58), an outlet (56) and a vent (66), the inlet (58) being operatively connectable, in use, to an aspirator tube; the outlet (56) being operatively connectable, in use, to a syringe (82); and the vent (66) comprising a one-way valve (70) permitting, in use, the flow of a fluid out of the three-way connector (51), wherein the inlet (58) comprises a receptacle (60) containing a porous or perforated element (62) which, when dry, permits the flow of gasses into the three-way connector (51), but which when wetted by a liquid, inhibits or prevents the flow of liquid into the three-way connector (51).

20 Claims, 3 Drawing Sheets

(51) Int. Cl.
*A61M 39/22* (2006.01)
*A61B 10/02* (2006.01)
*A61B 5/145* (2006.01)
*A61J 15/00* (2006.01)
*A61M 39/24* (2006.01)
*A61B 10/00* (2006.01)

(52) U.S. Cl.
CPC .......... *A61B 10/02* (2013.01); *A61B 10/0283* (2013.01); *A61J 15/0003* (2013.01); *A61J 15/0015* (2013.01); *A61M 1/007* (2014.02); *A61M 1/0023* (2013.01); *A61M 1/0025* (2014.02); *A61M 1/0052* (2014.02); *A61M 1/0066* (2013.01); *A61M 1/0086* (2014.02); *A61M 39/10* (2013.01); *A61M 39/223* (2013.01); *A61M 39/24* (2013.01); *A61B 2010/0061* (2013.01); *A61M 2039/1083* (2013.01); *A61M 2039/1088* (2013.01); *A61M 2039/229* (2013.01); *A61M 2039/244* (2013.01); *A61M 2039/2493* (2013.01); *A61M 2205/3324* (2013.01); *A61M 2205/583* (2013.01); *A61M 2205/584* (2013.01); *A61M 2205/7536* (2013.01); *A61M 2230/20* (2013.01)

(56) References Cited

U.S. PATENT DOCUMENTS

| | | | | |
|---|---|---|---|---|
| 3,650,093 | A | * | 3/1972 | Rosenberg .......... A61M 1/0005 96/6 |
| 4,078,563 | A | * | 3/1978 | Tuseth .................. A61M 5/40 137/192 |
| 5,125,415 | A | * | 6/1992 | Bell .................. A61M 5/3145 215/DIG. 3 |
| 6,019,899 | A | * | 2/2000 | Webb ................ B01D 19/0031 210/321.75 |
| 2009/0326483 | A1 | * | 12/2009 | Green .............. A61M 25/0017 604/247 |
| 2010/0041131 | A1 | * | 2/2010 | Brown .................. B01L 3/0206 435/309.1 |
| 2012/0016266 | A1 | | 1/2012 | Burkholz |
| 2013/0172781 | A1 | * | 7/2013 | Russo ................ A61B 5/14507 600/584 |

* cited by examiner

ASPIRATORS

This invention relates to aspirators, and in particular, but without limitation, to aspirators suitable for drawing fluids from within a body cavity of a human or animal patient.

Aspirators are used in a range of medical procedures where fluids need to be drawn from within a body cavity, for diagnostic, sampling and/or therapeutic purposes.

Pumped aspirators generally comprise a vacuum pump connected to a tube that can be inserted, or fed, into a body cavity, such that when the pump is switched on, the vacuum from the pump draws fluid from the body cavity through the tube, provided, of course, that the tip of the tube is located within the fluid to be aspirated. A liquid trap is usually interposed between the tube and the vacuum pump to prevent aspirated liquids from being drawn into the pump, which could damage and/or contaminate the pump. When using a vacuum pump aspirator, care needs to be taken to ensure that the vacuum is not too high and that the quantity and rate of aspiration is monitored. Monitoring and control circuitry can often be used to facilitate this, as well as the manual interventions of an experienced operator.

Where only relatively small amounts of fluids need to be aspirated, it is commonplace for a practitioner to use a syringe-based aspirator instead of a vacuum pump-based aspirator. In such a situation, the syringe is emptied (i.e. its plunger depressed) before being connected to the end of an aspirator tube. Prior to this, of course, the aspirator tube will have been inserted into the body cavity in a known manner, i.e. by feeding the tube with a guide wire inserted into it for rigidity, and upon location of the tip of the tube at a desired location, withdrawing the guide wire to leave the end of the tube extending from the body. When the aspirator tube has been correctly inserted, its tip will be submerged in the liquid to be aspirated. It should then be a relatively straightforward task to connect a pump or a syringe to the free end of the aspirator tube to aspirate the liquid. In the case of a syringe-based aspirator, this is achieved by withdrawing the syringe's plunger, to create a vacuum in the tube, which vacuum can be used to aspirate the liquid.

Generally speaking, syringes are sterile, inexpensive, disposable items, and so the problem of drawing aspirated fluids into the syringe is not usually a problem, and thus, there is usually no need to guard and/or proof the syringe against liquid ingress, i.e. to provide a fluid trap or any controls. In fact, in most cases, a simple syringe connected to a flexible tube is usually all that is required, as well as a skilled operator, of course.

Despite their relative simplicity and low-cost, known syringe-based aspirators suffer from a number of problems:

First, if a medical practitioner attempts to aspirate fluids (in particular liquids), especially relatively viscous fluids, through a relatively long pipe, an over-sized syringe needs to be used. The reason for this is that, due to the nature of the relationship between volume and pressure of air, in an isothermal expansion process, the volume of the syringe needs to be considerably larger than the internal volume of the tube to achieve a sufficient vacuum to draw fluids along the tube, especially against the effects of air pressure and gravity, which also act upon the fluid to be aspirated.

Second, viscous liquids exert a hydrodynamic drag and, unless the internal sidewalls of the aspirator tube are hydrophobic (by which is generally meant: aspirated liquid-phobic) the aspirated fluid sticks to the sidewalls of the tube leading to drag also. What this means is that the vacuum provided by the syringe needs to be greater than for a non-viscous liquid.

Third, the volume of air within the tube needs to be aspirated as well as the fluid itself. This can be counteracted, to an extent, by using a narrower bore tube, but narrower tubes tend to be more susceptible to clogging and pinching off, as well as increasing the hydrodynamic drag of a viscous aspirated liquid: thus a compromise needs to be found in this regard.

The upshot of the above, is that, in practice, practitioners tend to require a syringe whose volume is a factor of 10 to 100 or so greater than the volume of fluid to be aspirated (for example, a 50 ml syringe for a drop of aspirated fluid, or a 100 ml syringe for few ml of aspirated fluid). However, larger syringes are more awkward to handle, are more expensive to buy, more bulky to store and transport, and tend to be in shorter supply in medical environments than smaller syringes.

Nevertheless, in many instances, even a 100× over-sized syringe is insufficient to aspirate fluids (especially liquids) during a first attempt (the first withdrawal of the syringe plunger) and if the first attempt is unsuccessful, the practitioner, using a syringe-type aspirator, has two options:

Firstly, the practitioner can: 1) pinch-off the tube (to preserve the vacuum within it); 2) disconnect the syringe from the tube; 3) depress the syringe plunger to empty the syringe; 4) reconnect the syringe to the tube; 5) release the pinch-off; and 6) re-attempt the aspiration. This is not generally considered to be good practice because the practitioner needs to perform the operation single-handedly because one hand is occupied with pinching-off the tube. This method also has the potential to introduce a finite risk of contamination because the act of disconnection means that the components can no longer be sterile.

Secondly, the practitioner can "blow back" through the tube, by depressing the syringe plunger, to empty the syringe and try again. This also is not generally considered to be good practice because it risks inflating the body part at the distal end of the tube and in any event, puts the procedure back to the beginning.

It will be appreciated that neither of the above workarounds are ideal, and a need therefore exists for an improved and/or an alternative type of type of syringe-based aspirator.

A first aspect of the invention provides a valve assembly comprising a three-way connector operatively interconnecting: an inlet, an outlet and a vent, the inlet being operatively connectable, in use, to an aspirator tube; the outlet being operatively connectable, in use, to a syringe; and the vent comprising a one-way valve permitting, in use, the flow of a fluid out of the three-way connector, wherein the inlet comprises a receptacle containing a porous or perforated element which, when dry, permits the flow of gasses into the three-way connector, but which when wetted by a liquid, inhibits or prevents the flow of liquid into the three-way connector.

A second aspect of the invention provides an aspirator comprising an aspirator tube operatively connected to the inlet of a valve assembly comprising a three-way connector, the three-way connector additionally comprising an outlet operatively connectable, in use, to a syringe; and a vent comprising a one-way valve permitting, in use, the flow of a fluid out of the three-way connector, wherein the inlet comprises a receptacle containing a porous or perforated element which, when dry, permits the flow of gasses into the three-way connector, but which when wetted by a liquid drawn through the aspirator tube, inhibits or prevents the flow of liquid into the three-way connector.

A third aspect of the invention provides an aspirator comprising an aspirator tube operatively connected to the inlet of a valve assembly comprising a three-way connector, the three-way connector additionally comprising an outlet connected to a syringe; and a vent comprising a one-way valve permitting, in use, the flow of a fluid out of the three-way connector, wherein the inlet comprises a receptacle containing a porous or perforated element which, when dry, permits the flow of gasses into the three-way connector, but which when wetted by a liquid drawn through the aspirator tube, inhibits or prevents the flow of liquid into the three-way connector.

The configuration of the invention, as shall be described below, enables a conventional syringe to be able to act as a pump, whereby, upon raising the plunger, fluid (gas, air or liquid) can be drawn up the aspirator tube, but on depressing the syringe's plunger, fluid within the syringe and three-way connector is expelled via the vent. The invention is distinguished over known three-way connectors by its specific configuration.

Examples of known, similar types of dual check valve that are sometimes used in infusion procedures, include Borla SpA's (IT) "4166", "4419", "4687" and "4688" anti-gravity and anti-siphon check valves, an example of which is shown in FIG. 1 of the drawings.

In FIG. 1, the known three-way connector 10 is used as an in-line device and comprises a main body portion 12 having a hollow interior forming a three-way connector. The connector 10 comprises an inlet port 14, to which is connected in use, a tube leading from an IV drip. The connector 10 also comprises an outlet port 16 provided with a Luer lock connector, which connects to an IV giving line. Thus, fluids are able to flow from the IV drip bag to the giving line, and thence into the patient. A one-way check valve 18 is incorporated into the outlet port 16, which prevents siphoning of body fluids back into the IV drip bag, for example if the IV drip bag is located below the patient and, for example, to enable the IV drip bag to be disconnected without blood or other body fluids flowing back up the giving line and out through the inlet port 14.

A side entry port 20 feeds into the main body portion 12 and is also provided with a second one-way check valve 22 that allows fluids to flow into the junction, but not back out of it. The side entry port 20 is also provided with a Luer connector to allow a syringe to be connected to it, so that, say liquid medication can be injected into the patient via the IV giving line. However, when the syringe (not shown) is disconnected, the second one-way check valve 22 prevents the fluid from the IV drip bag (connected to the inlet) from escaping via the side entry port 20.

The configuration of the inlet 14, outlet 16 and side entry ports 20; and the first 18 and second 22 check valves is such that the illustrated junction can only be used as an in-line device, which permits the introduction of fluids into the giving line. In fact, there is no way to connect a syringe or tubes to the known device to enable it to function to convert a syringe into a pump as does the invention.

The receptacle of the invention suitably comprises a hollow interior portion for containing a quantity of aspirated fluid and/or gas and/or air.

Returning now to the invention, the syringe, where provided, suitably has a capacity of less than or equal to 100 ml, but preferably of less than or equal to 50 ml, and most preferably, of less than or equal to 10 ml, 5 ml or 1 ml.

In an embodiment, the invention provides a simplification of known aspirators by virtue of the following:

Only one one-way valve is needed because the porous or perforated element is located at the inlet of the three-way connector. This means that when the syringe (or a connected syringe) is pumped up and down, fluid (i.e. aspirated gasses and fluids) are drawn up the aspirator tube (or connected aspirator tube) by the vacuum created by the syringe on the up-stroke. However, when the syringe (or connected syringe) is depressed, gas from within the syringe enters the three-way connector and has two possible exit routes: back through the porous or perforated element (i.e. back down the aspirator tube); our out through the vent via the one-way valve. Nevertheless, the porous or perforated element provides a finite resistance to fluid flow, which resistance is greater than that of the one-way vale at the vent of the device, thus the gas from with the syringe is expelled through the vent in preference to back down the aspirator tube because the expelled gas follows the "path of least resistance". By locating the porous or perforated element at the inlet of the device, this advantageously means that only one one-way valve is needed, which can simplify construction, rationalise the part count, and also reduce cost and complexity.

By locating the porous or perforated element at the inlet of the device, aspirated liquid is unable to enter the three-way connector because it is blocked by the porous or perforated element before it can do so. Thus, provided the receptacle is detachable from the remainder of the device, the reminder of the device can be re-used.

The receptacle of the invention comprises a porous or perforated element that permits air or gasses to enter the three-way connector, but which inhibits and/or prevents the passage of liquids into the three-way connector.

The porous or perforated element suitably comprises an air permeable membrane, which permits air to pass through it, but not fluids. The porous or perforated element is suitably manufactured of a material, such as paper, which when dry, comprises pores or perforations that allow air or gasses to pass through the material, but which, when wetted, for example by an aspirated liquid, the liquid closes the pores or perforations thereby preventing fluids (air and/or gas and/or liquid) to pass through it.

Such a configuration conveniently provides a self-closing valve that permits air or gasses to pass through it when dry, but which when the wetted, self-seals to prevent fluids from passing through it.

The porous or perforated element may be impregnated with a reagent or testing chemical that changes colour upon contact with a target substance. In such a situation, the porous or perforated element is suitably visible from without the receptacle, for example, through a viewing window or a transparent portion of the receptacle. Suitably, the testing chemical can test for the presence of a target substance, such as any one or more of the non-exhaustive list comprising: an acid, a base (alkali), carbohydrate, glucose, sugar, blood, iron, protein, ketone, bilirubin, urobilinogen, nitrates, leukocytes, etc.

The porous or perforated element, in certain embodiments of the invention, may be manufactured from litmus paper, which changes colour on contact with acids or bases. Using litmus paper as the porous or perforated element of the invention conveniently enables it to be used to test for the presence of stomach acid, for example, when the invention is used as an enteral aspirator or as part of an NG tube.

The receptacle of the invention may comprise a viewing window, and/or it may be at least partially manufactured of a transparent material, to permit the contents of the receptacle to be visually inspected from the outside of it.

The aspirator tube, where provided, is suitably a flexible tube, such as a plastics or rubber tube. The tube is suitably sterilisable. The tube is suitably an enteral aspirator tube or an NG tube.

The inlet, outlet and vent of the three-way connector suitably comprise connectors for releasably connecting items thereto, such a "Luer lock" connectors, bayonet-type fittings, screw threads, push-fit connectors, being either male or female. Such a configuration suitably facilitates attaching and detaching items to the three-way connector.

Suitably, the inlet comprises a connector for connecting the inlet to the connector of enteral or NG tube, such as a female Luer-lock connector.

Suitably, the outlet comprises a connector suitable for connecting it to an enteral syringe, such as a male Luer or Luer-lock connector.

In an embodiment of the invention, the valve assembly effectively converts any standard syringe into a pump, allowing the piston to be pulled up and down repeatedly to pump fluid up the tube and into the receptacle. Such a configuration suitably avoids having to use an over-sized syringe to aspirate fluids and/or it suitably avoids the "disconnection-contamination", and "blowback" problems outlined above.

A further possible advantage of the invention is that it effectively converts a syringe into a pump without the need for a dedicated electric pump unit, per-se. In other words, the invention can provide an inexpensive and/or disposable alternative to, e.g. an electric pump, which electric pump would be overkill where only a small volume of sample is required.

Preferred embodiments of the invention shall now be described, by way of example only, with reference to the accompanying drawings in which.

Figure 1:
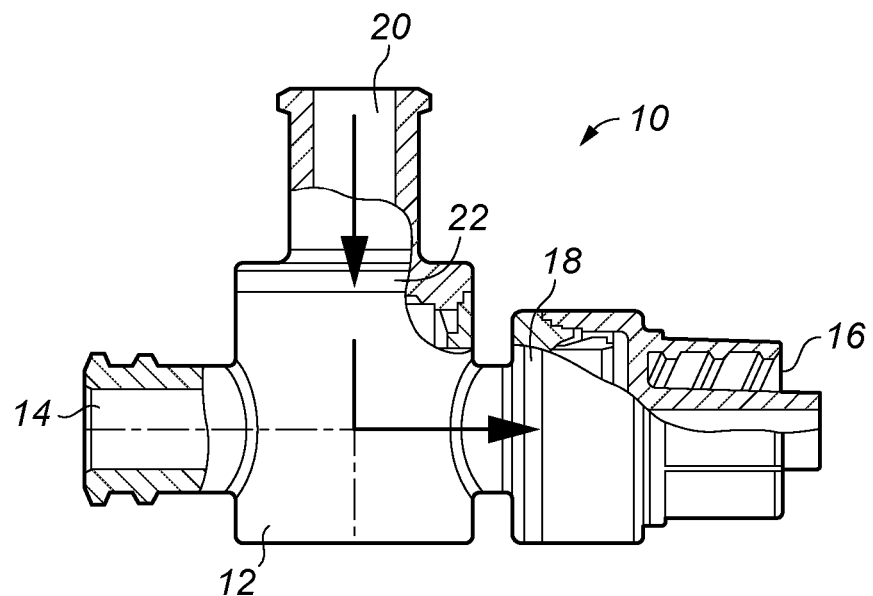
FIG. 1 is a partial lateral cross-section through a known three-way medial connector.

Referring now to FIGS. 2 to 5 of the drawings, a valve assembly 50 in accordance with the invention comprises a main body portion 52 comprising a straight-through tube 54 and a right-angled spur tube 56 extending from the straight-through tube 54 to form a three-way connector 51. The left hand end (in the drawings) of the straight-through tube 54 terminates in an inlet 58 for the valve assembly, which is connected, in use (although not shown in FIGS. 2 to 5) to an aspirator tube. The inlet 58 has a hollow, cylindrical receptacle 60 containing a disc 62 of initially dry porous or perforated material which is sealingly mounted within the receptacle 62 to prevent fluid from bypassing the disc 62. In other words, fluid entering the valve assembly 50 via the inlet 58, as indicated by arrow 64, must pass through the pores or perforations of the porous or perforated disc 62.

Figure 2:
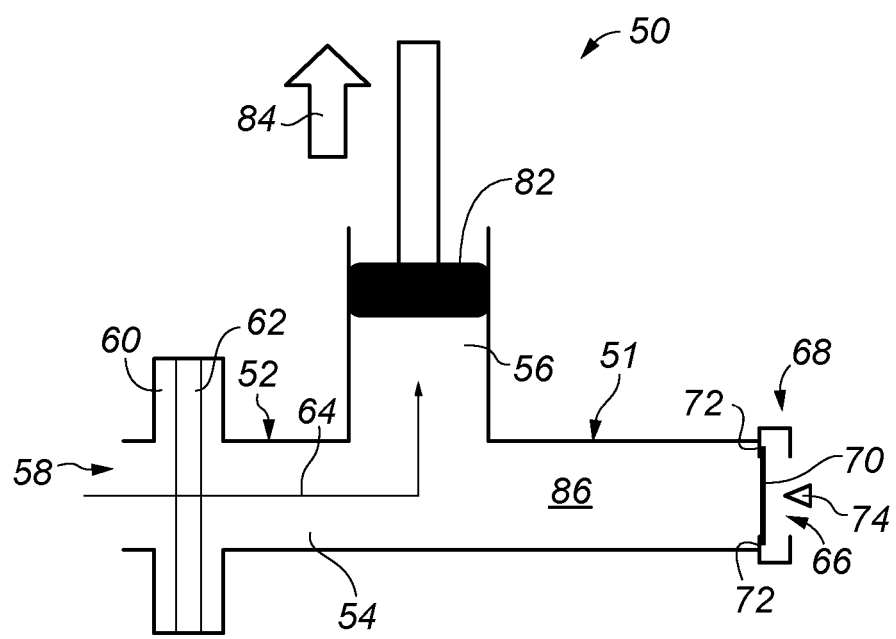
FIGS. 2 to 5 are a schematic series showing the operation of a valve assembly in accordance with the invention.

The right hand end (in the drawings) of the straight-through tube 54 forms a vent 66 for the valve assembly. A one-way valve 68 is located at the vent 66 and comprises a free floating disc 70 that is able to move between a sealing position (as shown in FIG. 2) where its periphery sealingly engages a peripheral edge 72 of the one-way valve 68, but which can move to an open position in which its periphery disengages the peripheral edge 72 of the one-way valve 68. The free floating disc 70 is retained within the one-way valve 68 by a cage or other retainer 74 indicated schematically in the drawings by the small triangle 74.

The right-angled spur tube 56 is in fluid communication with the straight-through tube 54 and its upper end (in the drawings) forms an outlet 76 that is connected to a syringe 78 comprising a chamber 80 and a plunger 82.

The valve assembly 50 is operated according to the sequence of FIGS. 2 to 5 as follows:

First, as shown in FIG. 2, the syringe plunger 82 is raised 84 creating a vacuum 86 within the tubes 54, 56 of the three-way connector 51. The vacuum 88 causes the one-way valve 68 to close resulting in fluids being drawn up the aspirator tube (not shown) towards the inlet 58 until the plunger 82 reaches the top of its stroke.

Figure 3:
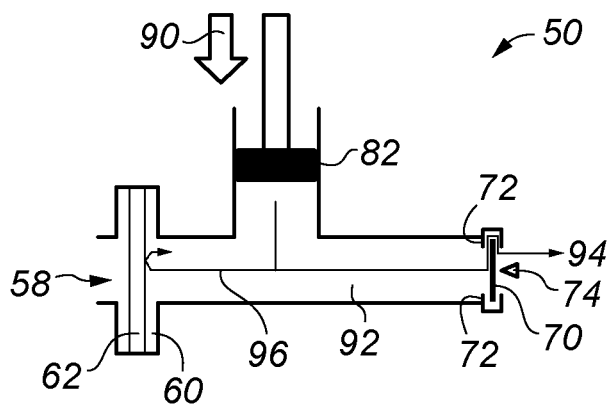

In FIG. 3, the plunger 82 is depressed 90 thus forcing aspirated fluid (gas/air) back into the tubes 54, 56 of the three-way connector 51, thereby pressurizing 92 it. The pressurised gas 92 can escape via the one-way valve (whose disc 70 now moves to the "open" position), as indicated by arrow 94. The pressurised gas 92 may also try to escape via the inlet 58 but the presence of the porous or perforated element 62 creates a finite resistance to such flow, as indicated by arrow 96, thus the pressurised gas 92 is vented via the vent 66 by following the "path of least resistance". In other words, because the resistance of the porous or perforated element 62 is greater than that of the one-way valve 68, the porous or perforated element 62 has surprisingly been found to function in a similar manner to a one-way valve, thus obviating an additional one-way valve at the inlet 58 of the valve assembly 50.

The raising 84 and depressing 90 of the syringe plunger 82 can be repeated, and the valve assembly 50 effectively converts the syringe into a pump for aspirating fluids.

Figure 4:
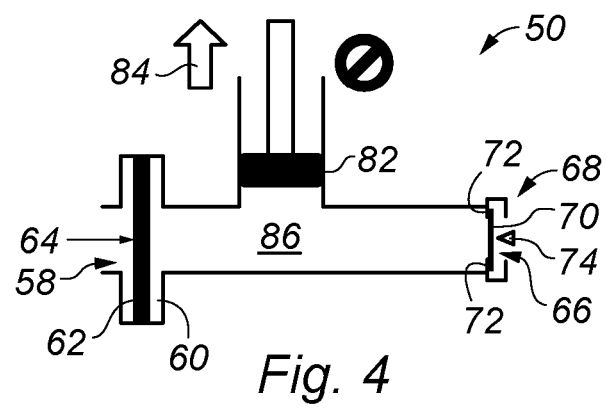
Figure 5:
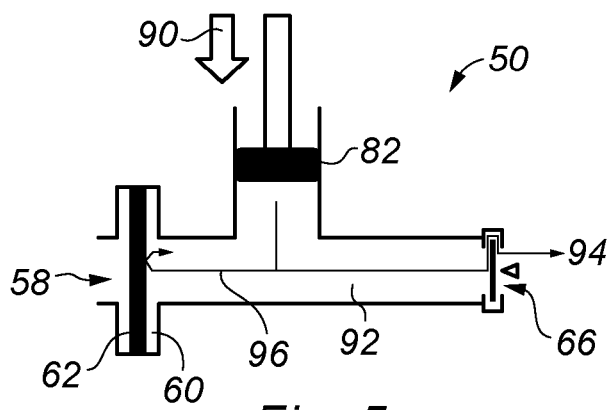

Eventually, some liquid may be aspirated, as shown in FIG. 4 and when this happens the porous or perforated element 62 becomes wet, thereby blocking its pores and/or perforations (as indicated by the black shading in FIGS. 4 and 5). This creates a blockage at the inlet 58 of the valve assembly thereby making it difficult for an operator to continue raising 84 the syringe plunger 82. This serves two useful and unexpected purposes: first, it provides a tactile feedback to an operator that the procedure is complete; and second, it prevents aspirated liquids (and indeed solids) from entering the main body 51 of the valve assembly where it could contaminate the syringe, block the tubes 54, 56 or block (i.e. hold open or hold closed) the one-way valve 68. This latter effect also means that the main body of the valve assembly, and the syringe, can be re-used provided the receptacle 60 is replaced, which reduces wastage.

If the operator continues to "pump" the syringe, as shown in FIG. 5 of the drawings, the blockage at the porous or perforated element 62 prevents 96 pressurised air 92 from being blown back down the aspirator tube (not shown) meaning that the pressurised air 92 can only be vented via the vent 66 as shown by arrow 94.

Figure 6:
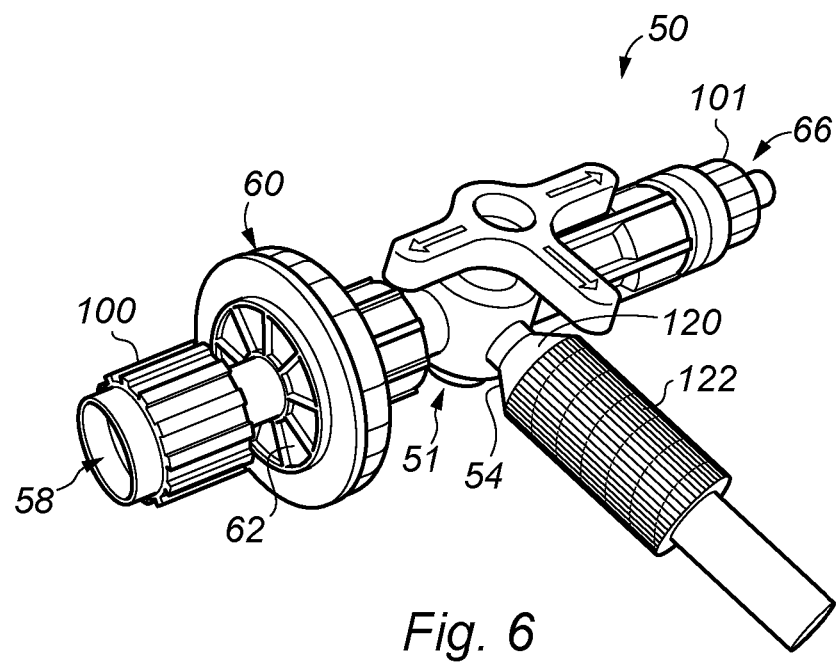
FIG. 6 is a perspective view of an embodiment of the invention.

FIG. 6 shows an embodiment of a three-way valve assembly 50 in accordance with the invention, which comprises a main body portion 51 forming the T-junction previously described. The valve assembly 50 has an inlet port 58 comprising a female Luer-lock connector 100 to which is connected, the male Luer-lock connector (not shown) of an enteral or NG tube (not shown).

The receptacle 60 is formed from a transparent plastics material, is interposed between the inlet port 58 and the main body portion 51. By making the receptacle 60 from a transparent material, the porous or perforated disc 62 within it is visible to an operator.

The vent 66 additionally comprises a Luer lock connector 101, although this is not absolutely necessary as it is unlikely that the aspirated gasses would need to be collected in everyday use, although there may be some medical tests where this is necessary.

Figure 7:
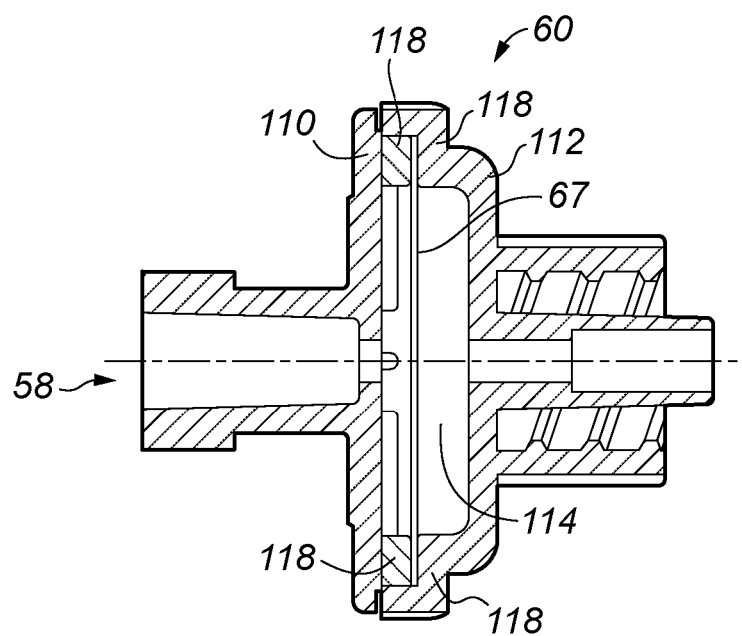
FIG. 7 is a cross-section through the receptacle shown in FIG. 6.

In FIG. 7 it can be seen that the receptacle 60 is formed from two components 110, 112 that snap together to form a hollow interior volume 114. The peripheral edges 116 of the two components 110, 112 each comprise an internal lip 118 that forms a pair of opposing abutment surfaces between which, when the two components are snap-fitted together, sealingly clamp the edges of the disc 62 in position.

The disc 62 is typically formed from indicator paper, such as litmus paper. When dry, the pores or perforations of the indicator paper permit air or other gasses to pass through it, but when wetted by aspirated liquids, the pores and/or perforations of the indicator paper become closed off as previously described.

Thus, the porous or perforated element 62 conveniently provides a self-closing valve that allows dry fluids to enter the receptacle 62, but which automatically closes-off when wetted.

Further, because at least one of the two component 110, 112 of the receptacle 60 are manufactured from a transparent plastics material, the colour of the indicator paper disc 62 can be readily inspected by a user. Thus, colour changes in the indicator paper 62, indicating the presence or absence of certain target substances (e.g. stomach acid) can be readily determined by visual inspection.

The outlet 56 of the valve assembly 50 comprises a male Luer-lock connector 120 that engages with a complementary female Luer connector (not shown) of a syringe. An internally screw-threaded locking barrel 122 is also provided on the outlet 56, which screw-threading engages with a complementary external screw thread of a syringe tip (not shown). The syringe (not shown) typically comprises a plunger 82 that sealingly and slidingly engages with the internal side wall of the syringe cylinder in a known manner.

In use, an enteral tube (not shown) is fed into a body cavity and its connector is connected to the connector 100 of the inlet 54 of the valve assembly 50. A syringe 96 is then connected to the outlet 54 of the valve assembly 50 using the barrel 122 previously described. This forms an aspirator in accordance with the invention.

The arrangement of the inlet, outlet and vent are not material to the operation of the invention: it will be readily apparent that outlet could be in-line with the inlet with the vent on the spur leg of the T-junction.

The aspirator tube (e.g. NG tube) can be inserted into a patient and an operator can then repeatedly depress and withdraw the syringe plunger 82 to create a vacuum 88 and over-pressure 92 within the aspirator to draw fluids up through the enteral tube on the up-stroke, and vent fluids (initially gasses) through the vent on each down-stroke. Eventually, a liquid may be aspirated from the body via the enteral tube, which liquid enters the receptacle via the inlet aperture thus wetting the indicator paper 62 and thereby providing a diagnostic test of the liquid (e.g. a check for stomach acid) whilst at the same time, automatically closing off the inlet aperture by wetting the indicator paper and clogging it in the manner previously described. At this point, the inlet is effectively "closed", thereby preventing or inhibiting further raising of the syringe plunger 82 and automatically indicating to the operator that the aspiration is complete. The blocking effect of the wetted porous or perforated element also provides that aspirated fluids are inhibited from, or cannot, be forced back down the enteral or NG tube, and therefore due to the one "way nature" of the device 50 it does not necessarily need to be sterile at the point of use, although sterilisation would, of course, be desirable in certain circumstances.

The invention thus provides a convenient solution to the problem of aspirating fluids and addresses one or more of the problems outlined above.

The invention is not restricted to the details of the foregoing embodiments, which are merely exemplary of the invention. For example, any shapes, sizes, relative dimensions etc. are illustrative, and not limiting, as are any material selections and/or design choices (e.g. type of check valve).

The invention claimed is:

1. A valve assembly (50) comprising a three-way connector (51) comprising and operatively interconnecting: an inlet (58), an outlet (56) and a vent (66), the inlet (58) being operatively connectable, in use, to an aspirator tube; the outlet (56) being operatively connectable, in use, to a syringe (82); and the vent comprising a single one-way valve (68) permitting, in use, the flow of a fluid out of the three-way connector (51), characterised in that the inlet (58) comprises a receptacle (60) containing a porous or perforated element (62) which, when dry, permits the flow of gasses into the three-way connector (51), but which when wetted by a liquid, inhibits or prevents the flow of liquid into the three-way connector (51), wherein the resistance of the porous or perforated element (62) is greater than that of the one-way valve (68).

2. The valve assembly (50) of claim 1, wherein the receptacle (60) comprises a hollow interior portion for containing a quantity of aspirated fluid and/or gas and/or air.

3. The valve assembly (50) of claim 1, wherein the receptacle (60) comprises a viewing window.

4. The valve assembly (50) of claim 1, wherein the receptacle (60) is at least partially manufactured of a transparent material.

5. The valve assembly (50) of claim 1, wherein the receptacle (60) comprises two components that snap together to form a hollow interior volume, the peripheral edges of the two components each comprising opposing abutment surfaces between which, when the two components are snap-fitted together, the porous or perforated element (62) is sealingly clamped.

6. The valve assembly (50) of claim 1, wherein the receptacle (60) is detachable from the remainder of the device.

7. The valve assembly (50) of claim 1, wherein the porous or perforated element (62) is manufactured of paper or card, which when dry, comprises pores or perforations that allow air or gasses to pass through the material, but which, when wetted, for example by an aspirated liquid, the liquid closes the pores or perforations thereby preventing liquids to pass through it.

8. The valve assembly (50) of claim 1, wherein the porous or perforated element (62) is impregnated with a reagent or testing chemical.

9. The valve assembly (50) of claim 8, wherein the reagent or testing chemical is one that changes colour upon contact with a target substance.

10. The valve assembly (50) of claim 9, wherein the target substance is any one or more of the group comprising: an acid; a base (alkali); carbohydrate; glucose; sugar; blood; iron; protein; ketone; bilirubin; urobilinogen; nitrates; and leukocytes.

11. The valve assembly (50) of claim 9, wherein the porous or perforated element (62) is manufactured from litmus paper, which changes colour on contact with acids or bases.

12. The valve assembly (50) of claim 1, wherein the inlet (58), outlet (56) and vent (66) of the three-way connector (51) comprise connectors for releasably connecting items thereto.

13. The valve assembly (50) of claim 12, wherein the connectors comprise any one or more of the group comprising: a Luer lock connector; a bayonet-type fitting; a screw thread; and a push-fit connector.

14. The valve assembly (50) of claim 12, wherein the inlet comprises a female Luer-lock connector.

15. The valve assembly (50) of claim 12, wherein the outlet comprises a male Luer or Luer-lock connector.

16. The valve assembly (50) of claim 12, wherein the vent comprises a Luer lock connector.

17. The valve assembly (50) of claim 1, wherein the one-way valve (68) comprises a free floating disc that is able to move between a sealing position where its periphery sealingly engages a peripheral edge of the one-way valve (68) and an open position in which its periphery disengages the peripheral edge of the one-way valve (68).

18. The valve assembly (50) of claim 1, wherein the capacity of the syringe is substantially equal to or less than any one of: 100 ml; 50 ml; or 10 ml.

19. The valve assembly (50) of claim 1, wherein the capacity of the syringe is substantially equal to or less than 5 ml.

20. An aspirator comprising an aspirator tube operatively connected to the inlet, and a syringe (82) operatively connected to the outlet (56) of, the valve assembly (50) of claim 1.

* * * * *